(12) United States Patent
Ganguly et al.

(10) Patent No.: US 10,695,020 B2
(45) Date of Patent: Jun. 30, 2020

(54) SYSTEMS, METHODS, AND DEVICES FOR MULTI-ENERGY X-RAY IMAGING

(71) Applicant: VARIAN MEDICAL SYSTEMS, INC., Palo Alto, CA (US)

(72) Inventors: Arundhuti Ganguly, San Jose, CA (US); Gary F. Virshup, Cupertino, CA (US); Michelle Richmond, Palo Alto, CA (US); Billy Dan Jones, Los Altos, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 345 days.

(21) Appl. No.: 15/601,068

(22) Filed: May 22, 2017

(65) Prior Publication Data

US 2018/0199904 A1    Jul. 19, 2018

Related U.S. Application Data

(60) Provisional application No. 62/446,246, filed on Jan. 13, 2017.

(51) Int. Cl.
| | |
|---|---|
| *A61B 6/00* | (2006.01) |
| *H05G 1/58* | (2006.01) |
| *G21K 1/10* | (2006.01) |
| *H05G 1/60* | (2006.01) |
| *H01J 35/04* | (2006.01) |
| *G01N 23/04* | (2018.01) |

(Continued)

(52) U.S. Cl.
CPC .............. *A61B 6/484* (2013.01); *A61B 6/482* (2013.01); *G21K 1/10* (2013.01); *H05G 1/58* (2013.01); *H05G 1/60* (2013.01); *A61B 6/04* (2013.01); *A61B 6/50* (2013.01); *A61B 6/54* (2013.01); *G01N 23/00* (2013.01); *G01N 23/04* (2013.01); *H01J 35/045* (2013.01)

(58) Field of Classification Search
None
See application file for complete search history.

(56) References Cited

U.S. PATENT DOCUMENTS

| | | |
|---|---|---|
| 6,285,740 B1 | 9/2001 | Seely et al. |
| 6,683,934 B1 | 1/2004 | Zhao et al. |

(Continued)

OTHER PUBLICATIONS

International Search Report and Written Opinion dated Mar. 28, 2018, in International Patent Application No. PCT/US18/12194.

(Continued)

*Primary Examiner* — Hoon K Song
(74) *Attorney, Agent, or Firm* — SGPatents PLLC

(57) ABSTRACT

A system can have an x-ray source that generates a series of individual x-ray pulses for multi-energy imaging. A first x-ray pulse can have a first energy level and a subsequent second x-ray pulse in the series can have a second energy level different from the first energy level. An x-ray imager can receive the x-rays from the x-ray source and can detect the received x-rays for image generation. A generator interface box (GIB) controls the x-ray source to provide the series of individual x-ray pulses and synchronizes detection by the x-ray imager with generation of the individual x-ray pulses. The GIB can control x-ray pulse generation and synchronization to optimize image generation while minimizing unnecessary x-ray irradiation.

20 Claims, 7 Drawing Sheets

(51) Int. Cl.
 A61B 6/04 (2006.01)
 G01N 23/00 (2006.01)

(56) References Cited

U.S. PATENT DOCUMENTS

| | | |
|---|---|---|
| 7,502,443 B1 | 3/2009 | Haynes et al. |
| 7,561,665 B2 | 7/2009 | Dasani et al. |
| 7,826,587 B1 | 11/2010 | Langan et al. |
| 8,019,044 B2 | 9/2011 | Shkumat et al. |
| 8,311,185 B2 | 11/2012 | Seppi et al. |
| 9,415,240 B2 | 8/2016 | Jordan et al. |
| 9,530,196 B2 | 12/2016 | Virshup et al. |
| 2003/0176779 A1* | 9/2003 | Ghelmansarai ........ G01N 23/04 600/407 |
| 2005/0084073 A1 | 4/2005 | Seppi et al. |
| 2008/0232549 A1* | 9/2008 | Poorter ................ A61B 6/4035 378/98.9 |
| 2014/0270069 A1 | 9/2014 | Ganguly |
| 2014/0270074 A1 | 9/2014 | Shah |
| 2015/0245463 A1 | 8/2015 | Nighan et al. |
| 2015/0250444 A1* | 9/2015 | Tamura ................ A61B 6/585 378/19 |
| 2017/0065240 A1* | 3/2017 | Zou ........................ A61B 6/482 |

OTHER PUBLICATIONS

Virshup et al., "Dual-Energy X-ray Fluoroscopy Imaging System," *Medical Physics*, Jun. 2014, 41(6).

\* cited by examiner

SYSTEMS, METHODS, AND DEVICES FOR MULTI-ENERGY X-RAY IMAGING

CROSS-REFERENCE TO RELATED APPLICATIONS

The present application claims the benefit of U.S. application Ser. No. 62/446,246, filed Jan. 13, 2017, which is hereby incorporated by reference herein in its entirety.

FIELD

The present disclosure relates generally to x-ray imaging, and more particularly, to systems, methods, and devices for imaging using x-rays of different energy levels, for example, dual energy x-ray imaging.

SUMMARY

Embodiments of the disclosed subject, an imaging system uses x-rays of different energy levels to image a patient or object. The imaging system includes a customizable module, for example, a generator interface box (GIB), that controls and synchronizes various components of the imaging system, such that the patient or object can be sequentially exposed to x-ray pulses of different energies and the modulated x-rays passing through the patient or object can be detected to form a composite image. The components of the imaging system and control thereof by the GIB can provide for real-time imaging at the different energy levels.

In one or more embodiments, a system can include an x-ray source, an x-ray imager, and a generator interface box. The x-ray source can generate a series of individual x-ray pulses. The series can include at least a first x-ray pulse having a first energy level and a second x-ray pulse having a second energy level different from the first energy level. The x-ray imager is disposed so as to receive x-rays from the x-ray tube and to detect the received x-rays for image generation. The generator interface box is configured to control the x-ray source to provide the first and second x-ray pulses and to synchronize detection by the x-ray imager with generation of the individual x-ray pulses.

In one or more embodiments, a method includes, using a generator interface box, controlling an x-ray source to generate a series of individual x-ray pulses during respective image frames. The series can include at least a first x-ray pulse and a subsequent second x-ray pulse having a different energy level than that of the first x-ray pulse. The method can further include, using the generator interface box, synchronizing image readout by an x-ray imager with a readout period of each image frame. The method can also include, using a computer processing unit, processing signals from the x-ray imager during respective image frames to generate one or more images of a patient or object through which the first and second x-ray pulses have passed.

In one or more embodiments, there are provided a non-transitory computer-readable storage medium, upon which is embodied a sequence of programmed instructions for x-ray imaging, and a computer processing system that executes the sequence of programmed instructions embodied on the computer-readable storage medium. Execution of the sequence of programmed instructions can cause the computer processing system to control an x-ray source to generate series of individual x-ray pulses, and to synchronize image readout by an x-ray imager with a readout period of each image frame. The series can include at least a first x-ray pulse and subsequent second x-ray pulse having a different energy level than that of the first x-ray pulse.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

Embodiments of the disclosed subject matter can provide real-time multi-energy (e.g., dual energy) x-ray imaging. For example, in a dual energy configuration, two x-ray images can be rapidly acquired in succession at two different x-ray energies (i.e., x-ray tube peak kilo voltage (kV or kVp) settings or even MeV settings). X-ray beams of higher energy (e.g., 100-150 kVp) are relatively more penetrating but produce less contrast, because there is greater attenuation in radio-opaque objects (e.g., bone) but little attenuation in soft tissue. X-ray beams of lower energy (e.g., 50-100 kVp) are relatively less penetrating but produce higher contrast, because there is significant attenuation from both soft tissue and radio-opaque objects. By combining images acquired using x-ray beams of different energies, visualization of specific features can be improved, e.g., by removing soft tissue from an image to emphasize radio-opaque structures or by removing radio-opaque features from an image to emphasize soft tissue features. For example, the dual images can be processed together to form a third image that highlights one tissue or material type over another, thereby allowing visualization of anatomy or structure in an image that would otherwise be obscured or obstructed by overlaying anatomy or structure.

Fast switching between the x-ray energies used to generate the two images can prevent artifacts, for example, due to motion between images. Such motion can include, for example, external movement of the patient or object during imaging and interior motion of anatomy due to breathing or cardiac motion. In addition, larger separation between the x-ray energy levels used to generate the two images leads to improved tissue/material separation in the resulting images. Synchronization and hardware limitations may inhibit fast switching between such large energy separations; however, embodiments of the disclosed subject matter provide synchronization and hardware features that address such limitations, among other things, thereby enabling real-time multi-energy imaging.

Figure 1:
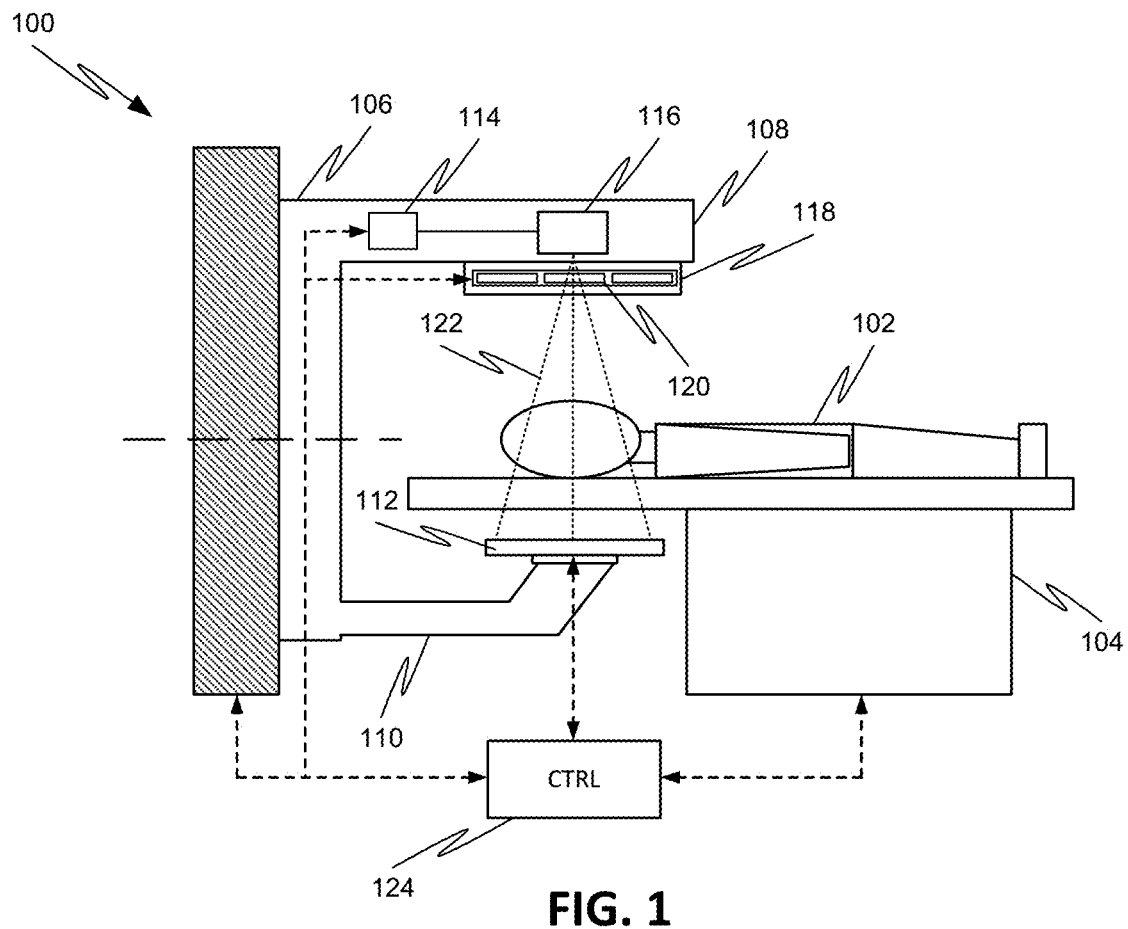
FIG. 1 illustrates components of an x-ray imaging system, according to embodiments of the disclosed subject matter.

Referring to FIG. 1, an exemplary x-ray imaging system 100 for real-time multi-energy (e.g., dual energy) imaging of a patient 102 (or other object) is shown. The patient 102 is held by support 104 (e.g., a treatment bed/couch or imaging conveyor belt) between an x-ray source on imaging head 108 and an x-ray imager on detection arm 110. The imaging head 108 and detection arm 110 can be supported by gantry 106, which can translate and/or rotate imaging head 108 and detection arm 110 to provide images at different orientations or locations within the patient 102. The gantry 106 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the imaging head 108 and detection arm 110 at various rotational and/or axial positions relative to the patient 102 may also be used.

For example, the imaging head 108 can include high voltage generator 114 that powers x-ray tube 116 to generate pulses 122 of x-rays to irradiate patient 102. For example, generator 114 can power x-ray tube 116 to generate at least a low energy x-ray pulse (e.g., 50-70 kVp) and a high energy x-ray pulse (e.g., 110-140 kVp) in quick succession (e.g., on the order of milliseconds). Other x-ray sources are also possible according to one or more contemplated embodiments. For example, x-ray tube 116 and/or generator 114 may be replaced by a linear accelerator (linac), a betatron, a synchrotron, or any other type of x-ray source.

The generation of alternating high and low energy x-ray pulses (or other intermediate energy level x-ray pulses) can be repeated to generate a pulse train of x-rays to provide continuous imaging of the same or different portions of patient 102. For example, each individual low energy x-ray pulse can be generated by applying a first voltage and/or current to the x-ray tube 116 via generator 114, and each individual high energy x-ray pulse can be generated by applying a second voltage and/or current to the x-ray tube 116 via generator 114. The second voltage/current can be higher than the first voltage/current, thereby creating x-rays of the relatively higher energy level. X-ray irradiation may cease (thereby defining an end of each pulse) by closing an aperture of the imaging head (not shown) or by modulating the voltage and/or current supplied to the x-ray tube 116 to a level insufficient to generate x-rays. In between pulses, the generator 114 may provide a voltage and/or current that is otherwise insufficient to generate x-rays. Alternatively, the voltage/current from generator 114 can be held constant between and/or during pulses, e.g., as described below with respect to FIGS. 5A-6B.

For each x-ray pulse, the resulting x-rays modulated by the anatomy of patient 102 can be received by imager 112 and can generate electrical signals indicative of the modulated x-rays. For example, the x-ray imager can be a flat panel detector or a combination of a scintillator/image-intensifier with photodetector array. The electrical signals can be conveyed from the imager 112 to a control module 124, for example, where the signals are processed to form respective images for each x-ray pulse. As noted above, the images obtained via the different energy level x-ray pulses can be combined together to form a composite image highlighting different materials or tissues. For example, the images can be combined via logarithmic subtraction after applying a weighting factor (see, for example, U.S. Pat. No. 8,019,044, entitled "Image acquisition for dual energy imaging," and incorporated by reference herein).

The imaging head 108 can further support beam modification module 118, which may be used to change characteristics of the x-ray pulse emanating from x-ray tube 116. Beam modification module 118 can thus include collimators, filter elements, apertures, etc. For example, beam modification module 118 can include an array of switchable filter elements 120 that can be moved into the x-ray beam path on command, for example by control module 124. Control of the filter elements 120 may be synchronized with the particular x-ray pulses, such that beam modification module 118 adapts the filter elements 120 in the beam path based on the desired x-ray pulse energy to modify the energy spectrum thereof. When the low energy x-ray plus is desired, one of the filter elements 120 (or a particular configuration of multiple filter elements 120) can be moved into the beam path. When the high energy x-ray pulse is desired, another one of the filter elements 120 (alternatively, no filter elements 120 or another configuration of multiple filter elements 120) can be moved into the beam path. For example, a rapidly configurable beam modification module can include multiple overlapping leaves as switchable filter elements, as described in U.S. Publication No. 2014/0270069, entitled "Real-time moving collimators with x-ray filtering material," which is hereby incorporated by reference herein in its entirety.

Alternatively or additionally, a filter module (not shown) can be provided between patient 102 and the imager 112. In such a configuration, the modulated x-rays emanating from patient 102 would pass through the selected filters before being detected by imager 112, thus altering the energy spectrum received by imager 112. As with the beam modification module 118, control of the filter module may be synchronized with the particular x-ray pulses, such that the filter elements in the modulated x-ray beam path are based on the desired x-ray pulse energy level. However, such a configuration may unnecessarily expose patient 102 to higher x-ray energy levels than would occur in the configuration of filter elements 120 between x-ray tube 116 and patient 102.

Operation of the different components of system 100 can be synchronized by controller 124. For example, controller 124 can control x-ray source 234 (e.g., generator 114, x-ray tube 116), and/or beam modification module 118 (e.g., by sending appropriate synchronization and/or command signals) to generate an x-ray pulse directed at a particular anatomy (e.g., by controlling support 104 and gantry 106 to direct the x-ray radiation at the desired location). At a same time, control module 124 can further control operation of imager 110 (e.g., by sending an appropriate synchronization signal thereto) such that exposure and read-out windows coincide with x-ray on and off periods associated with each x-ray pulse.

The controller 120 can include a computer with typical hardware such as a processor, and an operating system for running various software programs and/or communication applications. The computer can include software programs that operate to communicate with components internal to system 100, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, trigger hand switch, etc. The computer can also be networked with other computers and imaging systems. Both imaging system 100 and controller 124 can communicate with a network as well as databases and servers. The controller 124 can be configured to transfer image related data between different pieces of equipment.

The system 100 can also include a plurality of modules containing programmed instructions (e.g., as part of controller 124, or as separate modules within system 100, or integrated into other components of system 100), which instructions cause system 100 to perform different functions related to multi-energy imaging, as discussed herein, when executed. For example, system 100 can include image processing and synchronization modules that provide real-time multi-energy imaging. The modules can be written in C or C++ programming languages, for example. Computer program code for carrying out operations as described herein may also be written in other programming languages.

Figure 2:
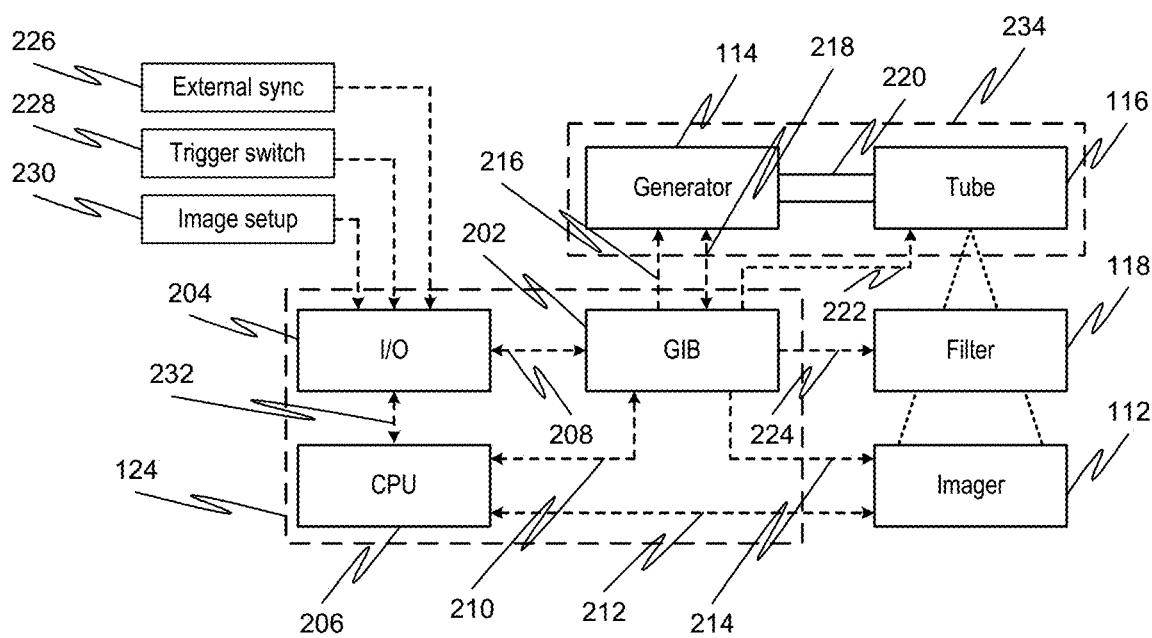
FIG. 2 is a simplified schematic diagram illustrating setup of various components and modules of an x-ray imaging system, according to embodiments of the disclosed subject matter.

Referring to FIG. 2, a simplified schematic diagram illustrating setup of system 100 components and modules is shown. As noted above, controller 124 can be operatively connected to various components of system 100 to control and synchronize operation thereof. In embodiments, controller 124 includes generator interface box (GIB) 202, input/output (I/O) module 204, and computer processing unit (CPU) 206. I/O module 204 can communicate with GIB 202 via communication line 208 and/or CPU 206 via communication line 232, for example, to convey one or more signals from external to controller 124. Such signals can include, but are not limited to, an external sync signal input 226 (e.g., a breathing or cardiac signal from patient 202, a user-generated waveform, or other external signal), a trigger switch signal input 228 (e.g., a trigger command from a hand-switch activated by a user of system 100), and image setup 230 (e.g., patient or anatomy data that GIB 202 may use in controlling system operation). Other inputs and outputs (not shown) from I/O module 204 are also possible according to one or more contemplated embodiments.

CPU 206 can receive signals from imager 112, for example, via communication line 212 indicative of the x-ray radiation received by imager 112 for each x-ray pulse and can use said signals to generate respective images. For example, when a high energy x-ray pulse and a low energy x-ray pulse are used, the CPU 206 can form separate first and second images and then combine the first and second images into a third composite image. In some embodiments, CPU 206 combines data underlying the first and second images to form the third composite image without actually forming (i.e., storing) the first and second images. For example, CPU 206 can process the first and second images using logarithmic subtraction and/or weighting to generate the third composite image. Alternatively, image processing may be performed external to system 100, for example, by a remote processing unit (not shown) that communicates with controller 124 via I/O module 204.

In some embodiments, the first image acquired from the high energy x-ray pulse and the second image acquired from the low energy x-ray pulse can be corrected prior to combination. For example, the first and second images can be corrected using a pair of separately acquired flat field images (i.e., images taken with no object or patient in the beam path) in order to correct system non-uniformities. Alternatively or additionally, the first and second images can be corrected using the weighting method as described in U.S. Pat. No. 9,530,196, entitled "Reducing heel effect in dual energy x-ray images," which is hereby incorporated by reference herein in its entirety.

GIB 202 can be a microcontroller-based interface hardware and firmware that synchronizes operation of the different system 100 components to generate multi-energy x-ray images. Thus, GIB 202 may be operatively connected to one or more of x-ray source 234 (e.g., generator 114, x-ray tube 116), beam modification module 118, x-ray imager 112, pulse synchronization circuit (not shown, but can be integrated with GIB), I/O module 204, and CPU 206. For example, GIB 202 may be operatively connected to generator 114 via a sync line 216 and a communication line 218. A sync signal to coordinate operation (e.g., on-off timing) can be sent from GIB 202 to generator 114 via sync line 216, while communication line 218 may be used to provide two-way communication of other information (e.g., selection of x-ray energy level) between GIB 202 and generator 114. In addition, generator 114 can be connected to x-ray tube 116 via power supply lines 220, which can provide current and/or voltage to x-ray tube 116 in generating the specific x-ray pulses.

In some embodiments, GIB 202 may also be operatively connected to x-ray tube 116 via sync line 222, for example, when x-ray tube 116 includes one or more grids to control electron output from one or more filaments of x-ray tube 116 (see discussion of FIGS. 5A-6B below). GIB 202 can thus provide a signal to x-ray tube 116 to coordinate operation (e.g., on-off timing) and/or energy level selection via sync line 222.

Similarly, GIB 202 can be operatively connected to beam modification module 118 and imager 112 via communication line 224 and sync line 214, respectively. The sync signal to coordinate operation (e.g., on-off timing) can be sent from GIB 202 to imager 112 via sync line 214 in order to coordinate read-out timing of the imager 112 with timing of the x-ray pulse from tube 116. Communication line 224 may be used to send a signal from GIB 202 to beam modification module 118 in order to select a particular filter element 120 configuration corresponding to the x-ray pulse to be generated by x-ray tube 116.

GIB 202 can also be operatively connected to CPU 206, for example, via communication line 208 (e.g., a serial connection). GIB 202 and CPU 206 may communicate with each other to coordinate aspects of the imaging process. For example, CPU 206 may process signals from imager 112 to form images for each x-ray pulse. In some embodiments, GIB 202 can terminate a particular x-ray pulse earlier than planned if sufficient image quality is otherwise already achieved, as discussed below with respect to FIG. 7D. CPU 206 may thus be configured to send a signal indicative of sufficient image quality to GIB 202 via line 208 for pulse termination.

GIB 202 can synchronize operation based on an algorithm for selecting optimized imaging parameters in order to maximize information in the resulting images. For example, GIB 202 can be programmed to take into account constraints associated with each component (e.g., x-ray source switching capability, imager frame rate, filter switching capability, etc.) and to select the best parameters for imaging a specific object or anatomy. For example, the high and low energy settings (i.e., kVp) and exposure level (i.e., mAs) may be different depending on the anatomy being imaged (e.g., radiography versus mammography). GIB 202 can take these factors into account in optimizing operation and synchronization of system 100 components. Alternatively or additionally, GIB 202 can rely on predetermined recipes stored in a memory of the system (e.g., memory 314 in FIG. 3) to control and synchronize operation or can be programmed based on user input or other external input.

Although specific communication/sync lines have been illustrated in FIGS. 1-2 and discussed above, embodiments of the disclosed subject matter are not limited to the illustrated configurations for signal transmission between the different components. Indeed, signal transmission can be effected in many other configurations besides those specifically illustrated. For example, signal transmission between GIB 202 and x-ray tube 116 may be made via generator 114 or control of x-ray tube 116 may be accomplished solely via control of generator 114, in which case sync line 222 may be omitted. In another example, communication between components may be routed through other components or a common sync/communication line, such as by combining sync lines 216, 222, 224 between GIB 202 and the components of the imaging head 108 (e.g., generator 114, x-ray tube 116, and beam modification module 118).

Alternatively or additionally, signal transmission between GIB 202 and the different components can be performed wirelessly. Each component (e.g., x-ray source 234, beam modification module 118, and/or imager 112) and GIB 202 can have a wireless receiver and, optionally, a wireless transmitter (e.g., a transceiver). Data transmission between imager 112 and CPU 206 via communication line 212 may also be wireless. For example, such a wireless imager may be the PaxScan 4336W Digital Image Receptor (manufactured by Varex Imaging of Salt Lake City, Utah).

Figure 3A:
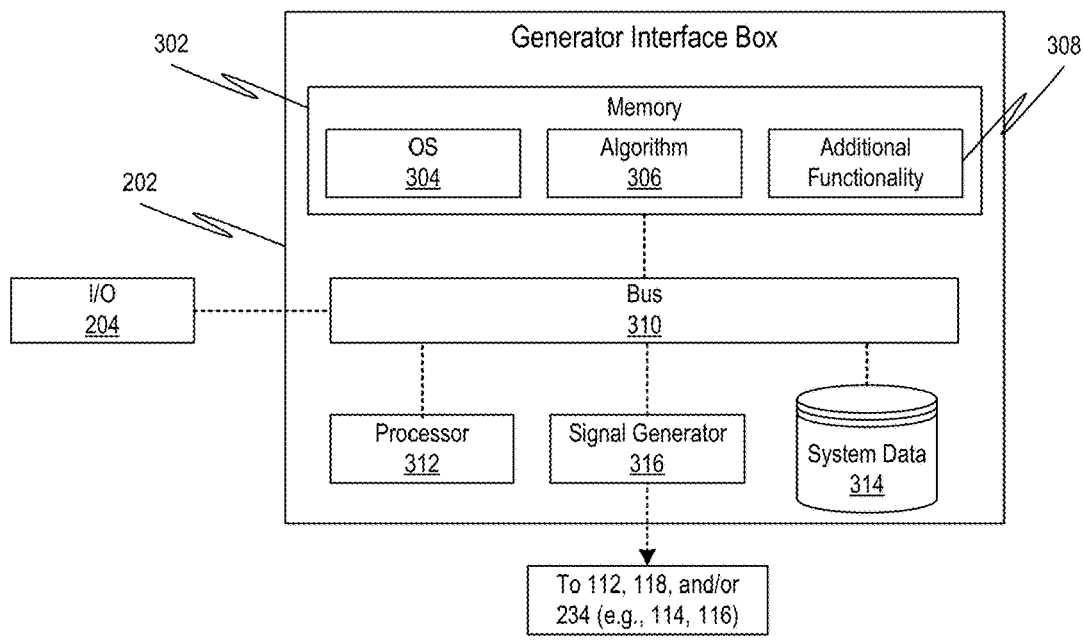
FIG. 3A is a simplified schematic diagram illustrating a generator interface box, according to embodiments of the disclosed subject matter.

FIG. 3A illustrates aspects of a system employing GIB 202 according to various embodiments of the disclosed subject matter. GIB 202 may include, for example, a computer system that can implement one or more aspects of the imaging and control processes described herein. Although shown as a single module 202, the functionality of module 202 can be implemented as a distributed system or otherwise.

For example, GIB 202 can include a bus 310 or other mechanism for communicating information between components. GIB 202 can also include a processor 312, for example, a general or specific purpose processor, coupled to bus 310. I/O module 204 can be coupled to GIB 202 and can be, for example, a communication device such as a network interface card that provides access to a network, and/or input/output ports that allow a user to interact with GIB 202, for example, via user input devices (e.g., mouse, keyboard, etc.) and a display. A user can thus interact with GIB 202 directly, remotely through a network, or via any other means.

GIB 202 can also include a memory 302 that stores information and instructions to be executed by processor 312. Memory 302 can be comprised of any combination of random access memory (RAM), read only memory (ROM), static storage such as a magnetic or optical disk, or any other type of computer readable media. For example, computer readable media may be any available media that can be accessed by processor 312 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 302 can store software modules that provide functionality when executed by processor 312. The modules can include, for example, an operating system 304, an algorithm module 306, and an additional functionality module 308. The operating system 304 can provide operating system functionality for the computer system of GIB 202. The algorithm module 306 can receive imaging setup data via I/O 204, can store the data in a database 314, can select the optimal parameters for imaging a specific object or anatomy while accounting for the constraints of each component of system 100, and/or can command signal generator 316 to generate sync or other command signals, for example, as described above and elsewhere herein. Alternatively or additionally, database 314 can include recipes or other data used in selecting parameters for components of system 100 or in generating the sync signals. Configurations and components for the GIB other than those illustrated in FIG. 3A are also possible according to one or more contemplated embodiments.

Figure 3B:
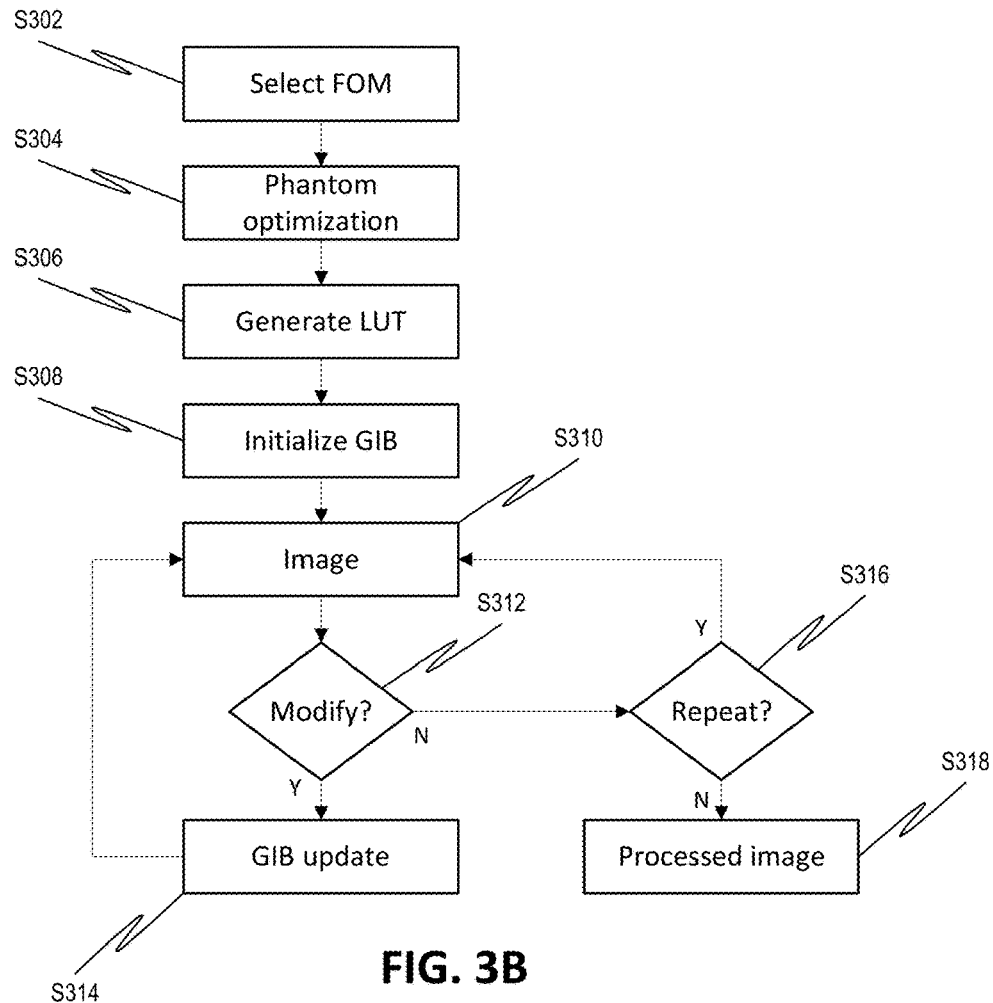
FIG. 3B illustrates a process flow employing a generator interface box, according to embodiments of the disclosed subject matter.

As noted above, the GIB 202 can employ an algorithm, for example, to select optimized imaging parameters in order to maximize information in the resulting images. The algorithm can be based on minimizing, or at least reducing, a radiation dose to the patient while maximizing, or at least increasing, the amount of information obtainable from the resulting images. FIG. 3B shows an exemplary process flow diagram for GIB 202 employing such an algorithm. Thus, at S302, a process can begin by selecting a figure of merit (FOM). Such FOMs can include, but are not limited to, signal-to-noise ratio (SNR), signal-to-dose ratio (SDNR), contrast-detail-to-dose (CDD), as well as other figures. The FOM may be selected by the GIB based on the type of imaging desired and/or treatment to be performed. Alternatively, or additionally, an operator of the imaging or treatment system may select an appropriate FOM.

The process proceeds to S304 where an anatomic phantom of different sizes are used to optimize imaging parameters. The safe working limits of the x-ray source (e.g., x-ray tube and corresponding generator) are known and provide boundaries for determining optimal imaging parameters. Using these working limits and by performing imaging of a variety of anatomic phantoms in a clinical setup, various combinations of tube current, voltage, and x-ray pulse time can be determined to yield the best results for the FOM selected. The results of the optimization of S304 can be stored in a look-up table (LUT) at S306, which can be input to the GIB 202 for use in determining optimal imaging sequences of high and low energy pulses. Such optimization S304 and LUT generation S306 may be performed prior to imaging of a patient, for example, at installation of the GIB system or on a periodic basis (e.g., daily, weekly, monthly, etc.).

When a patient is to be imaged, the GIB 202 can be initialized at S308 by selecting an imaging sequence from the LUT based on a phantom size therein closest to the anatomy being imaged and/or based on other factors (such as radiation treatment, movement of the anatomy, etc.). The GIB 202 can then control the various components of the imaging system to generate a pulse train of high energy and low energy pulses according to the selected imaging sequence in order to image the patient at S310.

The GIB 202 can also allow for modification of the x-ray pulse train or other parameters in real-time, based on feedback from analysis of the resulting images. For example, at S312, the GIB 202 can evaluated whether the x-ray pulse train should be modified. Thus, the GIB 202 can allow the parameters for the next x-ray pulse to be modified at S314 while the present x-ray pulse is being delivered. For example, the GIB 202 can monitor the FOM in real-time and can update the imaging sequence at S314 where the preselected values prove to be insufficient. The updated values for the imaging sequence may also be extracted from the LUT or otherwise determined by a formula. If the GIB 202 determines that the preselected values are sufficient based on monitoring of the FOM in real-time, then the GIB 202 may continue the pulse train at S316 for further imaging at S310 until it is desirable to terminate imaging, for example, by generating a final processed image at S318.

In addition to real-time modification of the x-ray pulse train for imaging, the GIB 202 can also provide real-time modification of other system parameters. For example, where the imaging system is coupled with a radiation treatment system, for example, to apply a treatment beam of radiation to an imaged tumor, the GIB 202 can suggest modification of the treatment beam in real-time based on dual energy x-ray image analysis.

Figure 4A:
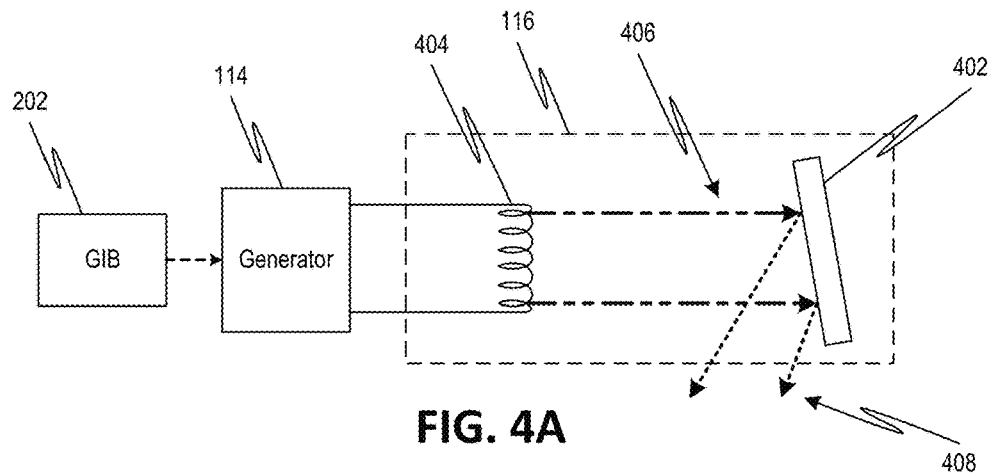
FIG. 4A illustrates a first configuration of an x-ray tube, according to embodiments of the disclosed subject matter.

Turning to FIG. 4A, a first configuration of an x-ray tube 116 that may be used in imaging system 100 is shown. X-ray tube 116 can include a cathode filament 404 spaced from an anode 402. When generator 114 applies an appropriate voltage/current to cathode filament 404, electrons 406 emanate from the cathode filament 404 and are accelerated toward anode 402. Impact of the electrons 406 with the anode 402 material generate x-rays 408 that form each x-ray pulse. However, such a configuration for x-ray tube 116 may be limited in how quickly it can switch between energy levels.

In particular, the x-ray tube 116 is limited by how quickly filament 404 can heat up or cool down to adjust to the next energy level for an upcoming x-ray pulse. The inability of the x-ray tube filament to adjust to each requested beam current in a pulse train may damage the x-ray tube and/or subject a patient to unnecessary x-ray exposure. Moreover, as the difference between energy levels for the x-ray pulse pairs is increased, the difference in filament 404 temperatures is similarly increased, thereby increasing a wait time between each pulse. For example, FIG. 4B shows a graph of beam current (Ib), voltage (kV), trigger signal (Trigger), and filament current (If) for a pulse pair having a low-energy pulse (Pulse 1) and a high-energy pulse (Pulse 2), for the scenario when heating begins at the start of each pulse. s illustrated in FIG. 4B, the filament current If is not able to adjust the filament temperature correctly due to its inherent time constant, thereby resulting in incorrect beam current Ib.

Figure 4B:
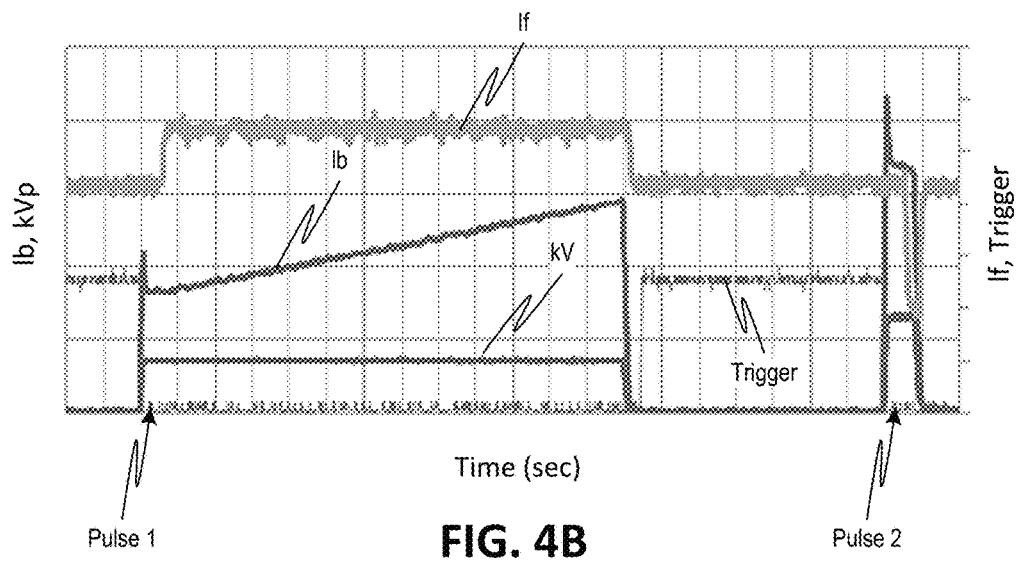
FIG. 4B is a timing diagram showing various waveforms for a dual-energy imaging system using an x-ray tube, where the filament current (If) is not able to adjust to filament temperature, thereby resulting in an incorrect beam current (Ib).

In particular, FIG. 4B shows the situation where the filament current returns to a baseline after exposure, which is optimal for neither the low kV pulse nor the high kV pulse. During exposure with the low kV pulse, the filament current (If) is increased at the start of the exposure in an attempt to get the beam current (Ib) to the requested value. The beam current (Ib) increases during the exposure as the filament heats up. After exposure, the filament current returns to the baseline. During exposure with the high kV pulse, the filament current is too high and the beam current becomes much higher than the requested amount. While the filament current is subsequently reduced, the reduction is too late to affect the beam current. Depending on the values, this incorrect x-ray output could have damaging consequences to both, the x-ray track and tube, and could also over-expose the patient to x-ray radiation.

Figure 4C:
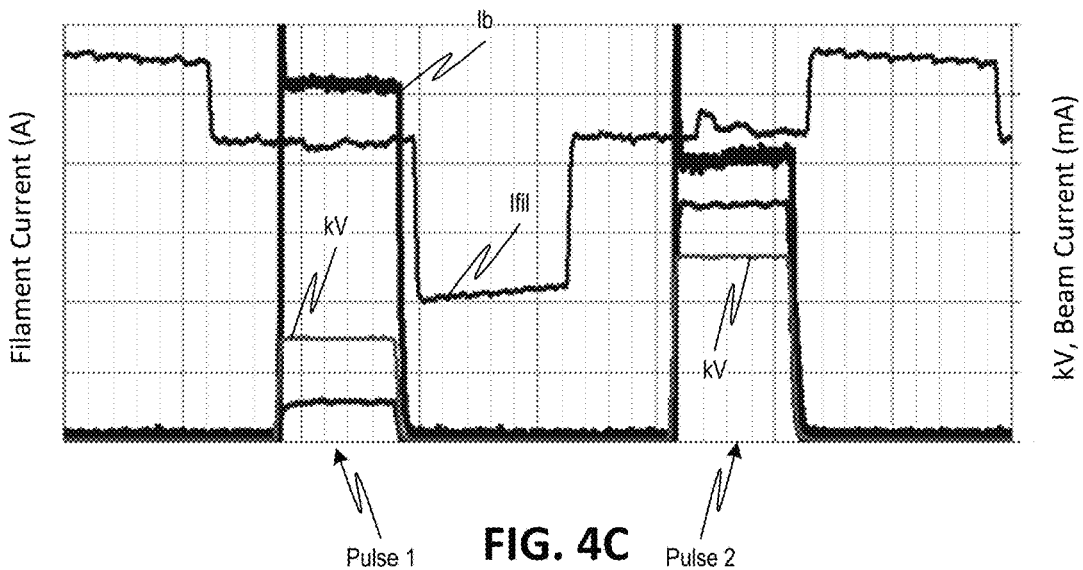
FIG. 4C is a timing diagram showing various waveforms for a dual-energy imaging system using an x-ray tube, wherein the filament current (Ifil) is able to adjust to the filament temperature, thereby resulting in the desired beam current (Ib).

To avoid incorrect beam currents, it is desirable to ready the x-ray tube filament for the upcoming pulse well before the start of the pulse (i.e., pre-heating) rather than at the start of the pulse. Pre-heating the filament to the correct temperature allows for the desired emission of electrons, which are then accelerated to hit the anode and make x-rays. This may further enhance the accuracy and repeatability of the x-ray output. Such a result is illustrated in FIG. 4C, where beam current (Ib), voltage (kV), and filament current (Ifil) for a pulse pair having a low-energy pulse (Pulse 1) and a high-energy pulse (Pulse 2), for the scenario where the temperature is raised to the correct intermediate and final state in between the two pulses. As illustrated in FIG. 4C, the correct filament output is obtained during the actual x-ray pulse.

In particular, FIG. 4C illustrates the scenario where the filament current is reset to either cool or heat the filament immediately after an exposure, i.e., in anticipation of the next exposure. For example, after exposure with the low kV pulse, the cathode filament may be too hot for the next requested exposure with the high kV pulse. Accordingly, the filament can be cooled for an appropriate period of time prior to the next exposure. After the high kV pulse, the cathode filament may be too cool for the next low kV pulse. Accordingly, the filament can be heated prior to the next exposure. Thus, in embodiments of the disclosed subject matter, the filament can be heated or cooled immediately after an exposure (or as soon as is feasible after an exposure) in preparation for the next exposure so that the beam current can be close to what is expected for that exposure. For example, such heating and cooling operations may be controlled by the GIB.

Figure 5A:
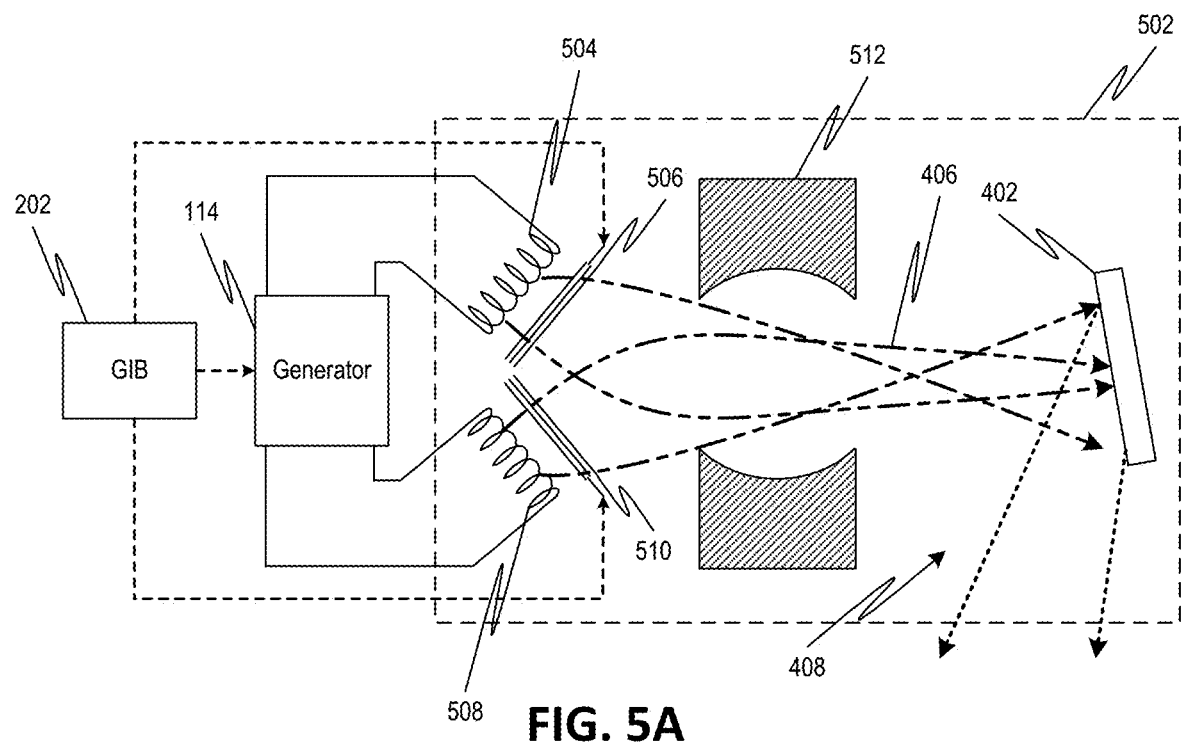
FIG. 5A illustrates a second configuration of an x-ray tube with both filaments generating an x-ray pulse, according to embodiments of the disclosed subject matter.
Figure 5B:
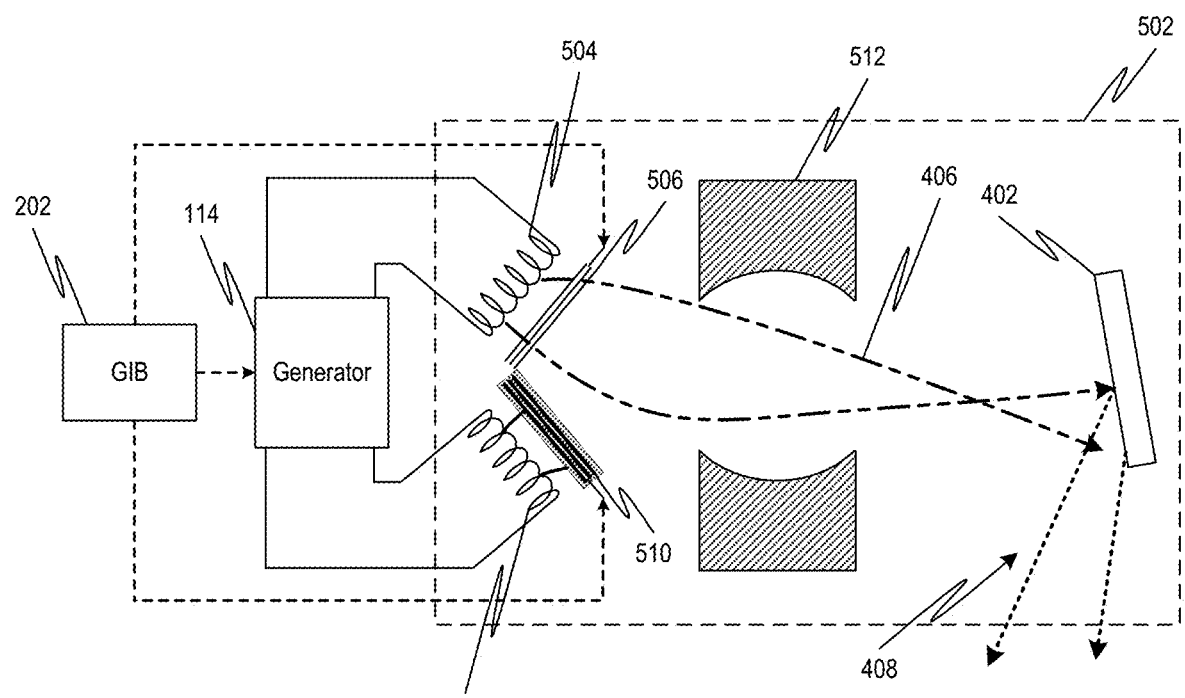
FIG. 5B illustrates the second configuration of an x-ray tube with a single filament generating the x-ray pulse, according to embodiments of the disclosed subject matter.

FIGS. 5A-5B illustrate a second configuration of an x-ray tube 502 that can be used to address the temperature induced switching limitations of FIG. 4A. In particular, x-ray tube 502 includes more than one cathode filament, for example, a first filament 504 and a second filament 508. Both filaments 504, 508 can be operatively connected to generator 114, which is controlled by GIB 202. In contrast to FIG. 4, the voltage/current applied by generator 114 to each filament 504, 508 does not change in order to generate the pulses of different energies. In other words, each filament 504, 508 is maintained at working current during each pulse (regardless of the energy level) and can optionally be maintained at working current between pulses.

Control of the energy of the resulting pulses is achieved by applying a voltage to one or more control grids, for example, a first control grid 506 disposed adjacent to the first filament 504 and a second control grid 510 disposed adjacent to the second filament 508. The voltage applied to the control grid can be controlled between levels that completely repel electrons ejected from the respective filament and levels that completely allow electrons to pass through to the anode. Thus, the bias level of the control grids can control the electron beam from the filaments and consequently the x-ray output of the x-ray tube 502. Operation of the control grids 506, 510 can be controlled by GIB 202.

In FIG. 5A, both control grids 506 and 510 are held a voltage that allows electrons 406 to pass to anode 402 via a focusing element 512 (e.g., focusing cup) to generate a high energy x-ray beam 408. In contrast, in FIG. 5B, control grid 510 is held at a voltage that repels electrons from filament 508, such that only electrons 406 from filament 504 are active on the anode 402, thereby generating a low energy x-ray beam 408. In a non-limiting simplified example to illustrate the above noted principles, each filament 504, 506 can be held at a working current effective to provide x-rays having an energy of 75 kVp. Thus, in the configuration of FIG. 5A, the x-ray beam produced by both filaments 504, 508 would have an energy of 150 kVp, and in the configuration of FIG. 5B, the x-ray beam produced only by filament 504 would have an energy of 75 kVp.

Figure 6A:
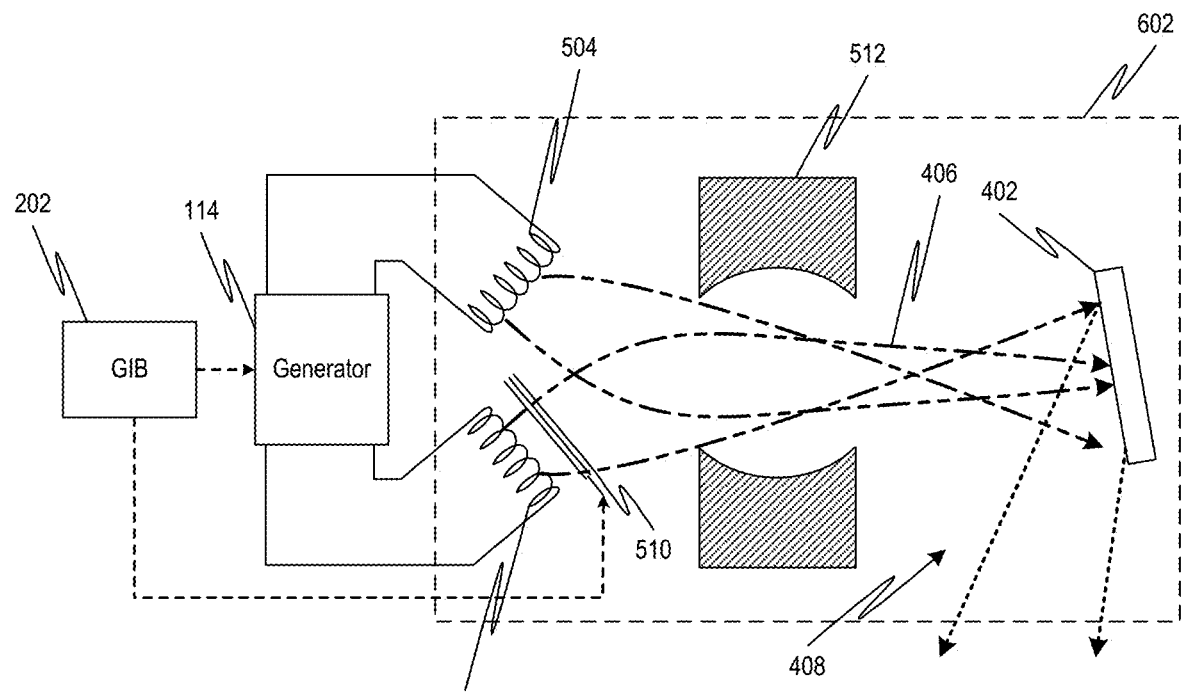
FIG. 6A illustrates a third configuration of an x-ray tube with both filaments generating an x-ray pulse, according to embodiments of the disclosed subject matter.
Figure 6B:
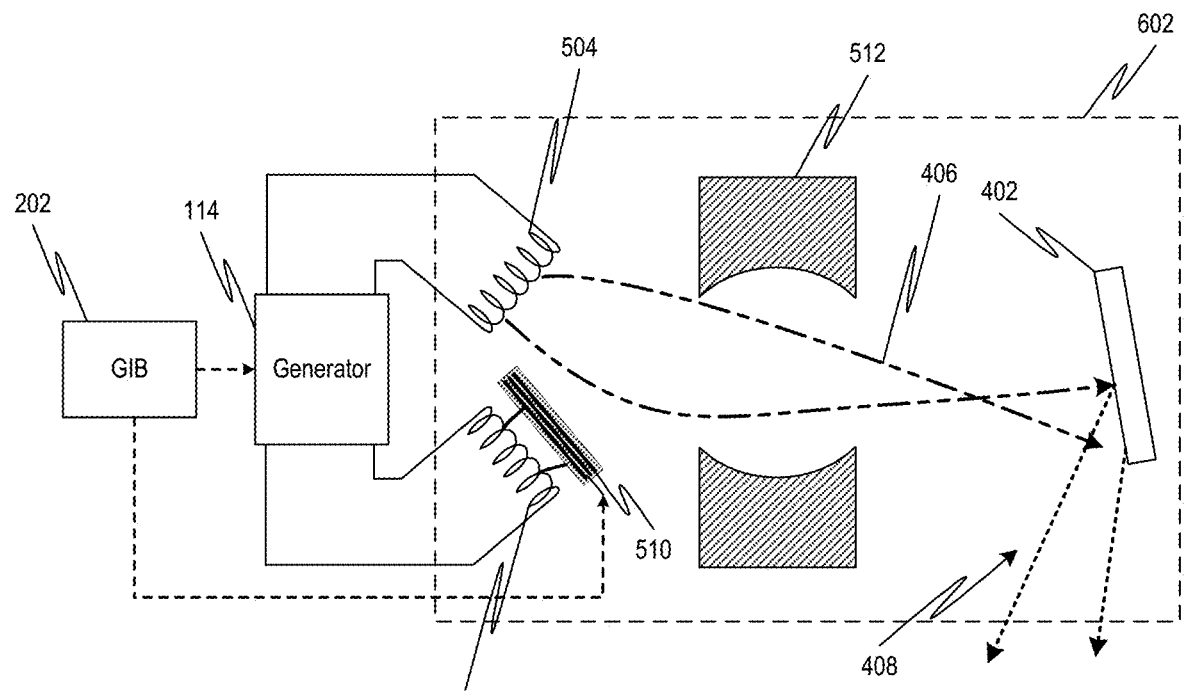
FIG. 6B illustrates the third configuration of an x-ray tube with a single filament generating the x-ray pulse, according to embodiments of the disclosed subject matter.

Other configurations employing grids and multiple filaments for enabling fast switching between x-ray energy levels are also possible according to one or more embodiments. For example, a single grid 510 could be used to switch between a configuration that generates a high energy x-ray pulse (FIG. 6A) and a configuration that generates a low energy x-ray pulse (FIG. 6B). The total electron beam current will be the sum of the filaments with and without the grid. Although FIGS. 5-6 illustrate only two filaments and corresponding control grids, embodiments of the disclosed subject matter are not limited thereto. Indeed, embodiments can include any number of filaments and/or control grids.

Moreover, it also possible for the control grids to be held at a voltage that partially allows electrons to pass to the anode, thereby reducing but not eliminating an electron beam from one (or both) of the filaments. In such a manner, the energy level of the resulting x-ray pulse can be quickly tuned without altering a working current applied to the filaments. In addition, although operation of the control grid has been discussed with respect to controlling x-ray pulse energy level, other applications within the context of the present system are also possible. For example, the voltage applied to the control grids can be used to turn off x-ray generation between pulses, e.g., by applying a voltage to each control grid 504, 510 in FIGS. 5A-5B to repel all electrons from respective filaments 504, 508.

Although FIGS. 5-6 illustrate GIB 202 as directly controlling grids 506, 510, embodiments are not limited to this specific configuration. Indeed, other configurations are possible according to one or more contemplated embodiments. For example, a separate generator may be interposed between GIB 202 and grids 506, 510. The separate generator could provide the required control voltages for grids 506, 510 responsive to an appropriate command signal from GIB 202. In another example, generator 114 can also be used to generate the necessary control voltages for grids 506, 510 based on command signals from GIB 202. Other configurations will be readily apparent to one of ordinary skill in the art and are within the scope of the present disclosure.

As noted above, a dual-energy pulse pair includes a first x-ray pulse having a relatively higher average x-ray energy and a second x-ray pulse having a relatively lower average x-ray energy. Images can be generated by the imaging system 100 for each x-ray pulse and combined together to generate a composite image. In general, an imaging sequence comprises a time window 704 during which exposure by the x-ray pulse occurs followed by a period 706 during which the imager (e.g., a digital x-ray detector) can read out the resulting image. Each x-ray on window 704 and corresponding read-out period 706 may comprise an image frame 702, which may be repeated in sequence to acquire multiple images, with the x-ray pulses in the image frames alternating between the different energy levels.

Figure 7A:
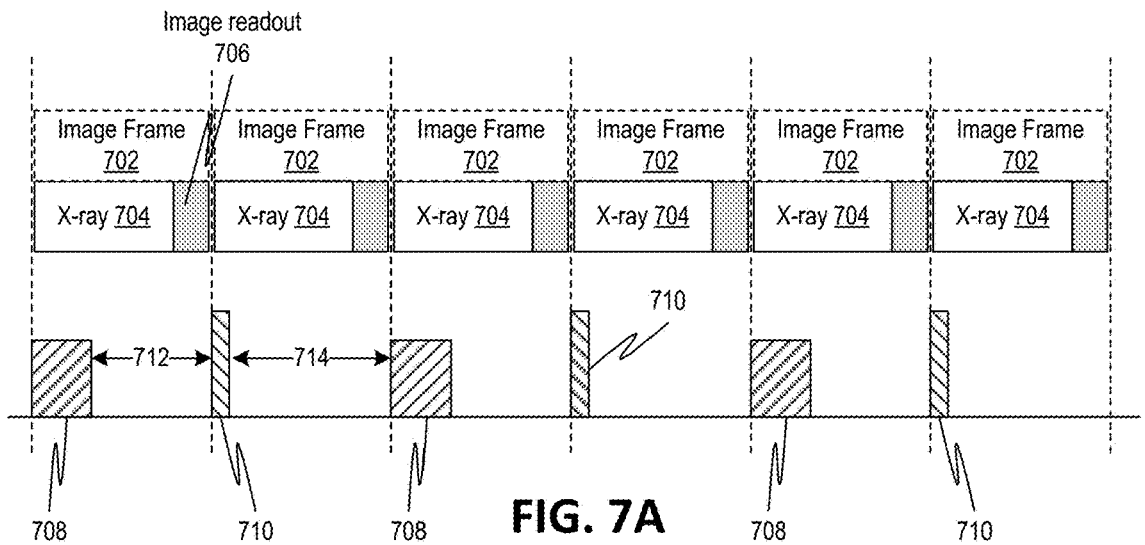
FIG. 7A is a timing diagram illustrating a default timing scheme in dual energy imaging, according to embodiments of the disclosed subject matter.

For example, a first image frame 702 may correspond to imaging using a low energy x-ray pulse 708 and an adjacent image frame 702 may correspond to imaging using a high energy x-ray pulse 710, as shown in FIG. 7A. For similar image signal-to-noise ratio, the higher energy x-rays can be on for a shorter time duration (i.e., smaller pulse width) than the lower energy x-rays. Thus, the pulse width for high energy x-ray pulse 710 is smaller than the pulse width for low energy x-ray pulse 708. The start of each image frame 702 (and the corresponding end of the readout period 706 of the immediately previous image frame 702) can correspond with initiation of the x-ray pulse for that image frame 702. Thus, a time interval 712 between an end of the low energy x-ray pulse 708 and a beginning of the next high energy x-ray pulse 710 is generally greater than a time interval 714 between an end of the high energy x-ray pulse 710 and a beginning of the next low energy x-ray pulse 708.

The gap between low energy x-ray pulse 708 and high energy x-ray pulse 710 (e.g., either interval 712 or interval 714) may influence image quality, since internal or external motion of the patient or object between timing of the x-ray pulses 708, 710 could lead to misregistration between images or other image artifacts. Thus, in embodiments, GIB 202 can control the generator and/or x-ray tube to minimize, or at least reduce, a gap between low and high energy x-ray pulses.

Figure 7B:
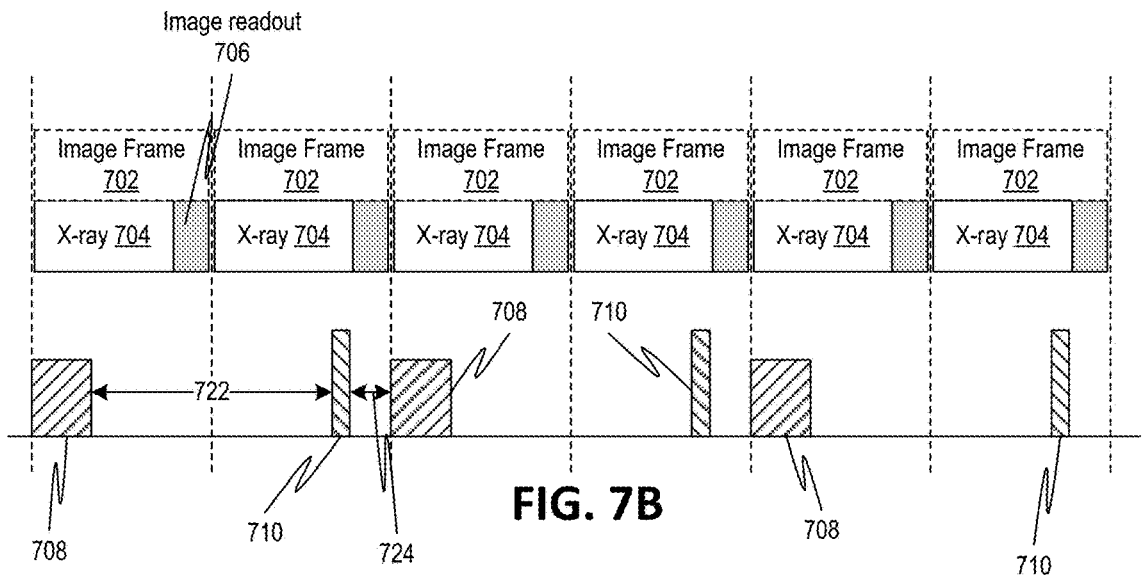
FIG. 7B is a timing diagram illustrating a timing scheme with shifted high energy pulses, according to embodiments of the disclosed subject matter.

For example, FIG. 7B shows an example of pulse shifting by GIB 202. In contrast to FIG. 7A, high energy x-ray pulse 710 has been shifted from the beginning of the x-ray on window 704 to an end period of the x-ray on window 704, such that the x-ray pulse 710 terminates just before the start of the image readout period 706. As a result, the interval 724 between the high energy x-ray pulse 710 and a subsequent low energy x-ray pulse 708 can be minimized, or at least reduced. For example, the interval 724 may be equal to or substantially equal to a time for the image readout period 706. Also, a time interval 722 between an end of the low energy x-ray pulse 708 and a beginning of the next high energy x-ray pulse 710 is generally less than a time interval 724 between an end of the high energy x-ray pulse 710 and a beginning of the next low energy x-ray pulse 708.

Although the high energy x-ray pulse 710 has been shifted to the end of the x-ray on window 704, it is also possible that the high-energy x-ray pulse 710 may be maintained at the start of the x-ray on window 704 and the low-energy x-ray pulse 708 instead be shifted to the end of the x-ray on window 704. In such a case, the minimum gap between a pair of low and high energy x-ray pulses 708, 710 will still be equal to or substantially equal to a time period of the image readout period 706. It is further contemplated that the low and high energy x-ray pulses 708, 710 may initiated/terminated at other timings within x-ray on window 704 than just the beginning or end of window 704, which timing control is enabled by the independent synchronization and fast switching features of GIB 202 and other components of the imaging system disclosed herein.

Figure 7C:
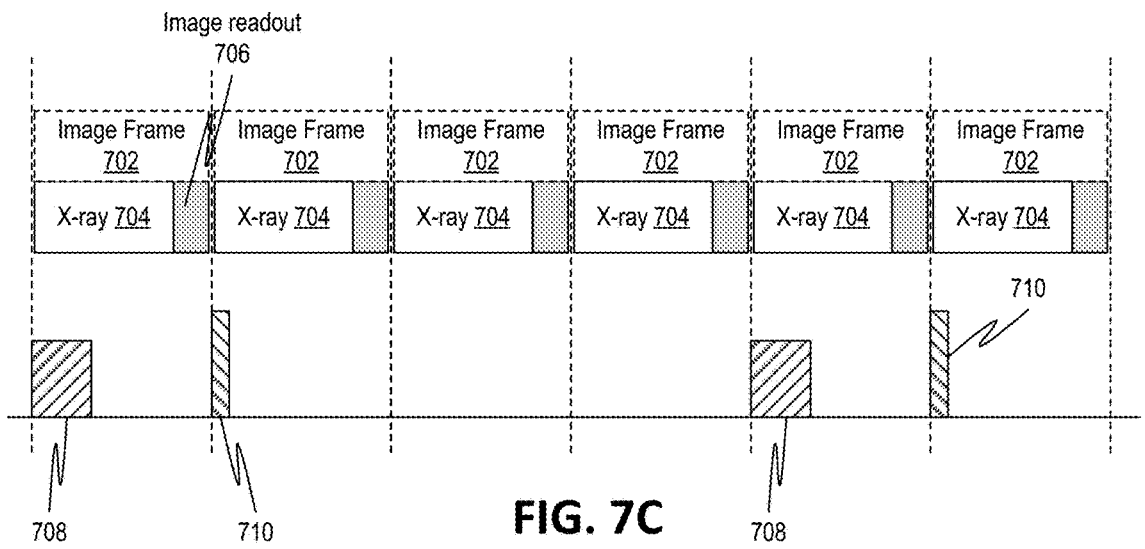
FIG. 7C is a timing diagram illustrating a timing scheme with pulse skipping, according to embodiments of the disclosed subject matter.
Figure 7D:
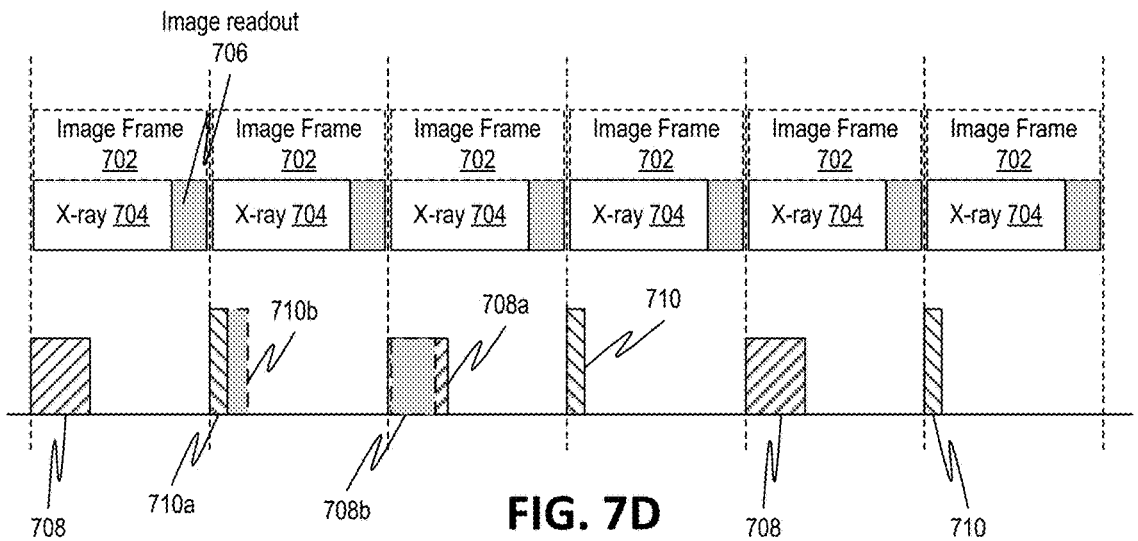
FIG. 7D is a timing diagram illustrating a timing scheme with pulse width variation, according to embodiments of the disclosed subject matter.

In some embodiments, GIB 202 can be configured to allow independent or dependent synchronization of the imager, for example, with respect to a respiration or cardiac signal, system status signals, a user-generated waveform, or any other signal. For example, in certain situations, it may be desirable to acquire images less frequently while keeping the readout window 706 at a minimum. GIB 202 can keep imager running at a certain frame rate (e.g., repeating image frame 702) while controlling the generator/x-ray tube to skip x-ray irradiation during certain frames, as illustrated in FIG. 7C. Such skipping may be at regular or irregular intervals, and may include pulse pairs (high and low energy x-ray pulses) or only one of the pulses of a particular pair. Images can be acquired by turning on x-rays only at desired times, while otherwise maintaining synchronization between the x-ray tube and imager.

For example, the GIB 202 can be configured to direct skipping of pulses during imaging with a rotating gantry. In general, it is beneficial to minimize the radiation dose applied to the patient while still achieving sufficient imaging resolution. However, when imaging with a rotating gantry, imaging at all angles may be unnecessary (e.g., duplicative of other imaging angles, or of poorer quality due to anatomy or system configurations). The GIB 202 can be programmed, or may recognize in real-time based on image feedback, that such angles can be skipped in the pulse train. The GIB 202 can then resume regular pulses within the pulse train once the gantry rotates to locations where imaging is again desired.

Alternatively or additionally, the GIB 202 can elect to skip pulses in the pulse train based on feedback from acquired images. For example, if an image shows that the signal is insufficient for clinical imaging and changing kV/mA/ms within the limits of operation of the x-ray tube are not possible, the next several pulses can be skipped until the analysis shows that the signal level can be restored. This may spare the patient from an otherwise unnecessary x-ray dose.

In some embodiments, GIB 202 can be programmed to start and/or stop each x-ray pulse as desired within a particular x-ray window. For example, after switching energy level or upon initiation of the x-ray pulse, the x-ray tube could take a finite time to settle on a desired output due to characteristic thermal delays of the x-ray tube filament. GIB 202 can control a termination of the x-ray pulse to be earlier or later than a predetermined time in response to system feedback. For example, pulse 710a can be extended within x-ray on window 704 to terminate later as shown by pulse outline 710b, while pulse 708a can be terminated earlier within x-ray on window 704 as shown by pulse outline 708a.

GIB 202 can control pulse termination responsive to desired image quality. Earlier termination may allow for more time for the filament to adjust to the next level before pulse initiation, while a later termination may accommodate output that is still adjusting at the beginning of the pulse. CPU 206 may process image signals provided during each image frame 704 and can provide a feedback signal to GIB 202, which may modify pulse widths in real time (e.g., during the image frame generating the feedback signal) or to adjust pulse widths for subsequent image frames (e.g., 708a being modified based on data acquired during prior pulse 708).

Although embodiments have been described above with respect to a standalone imaging system, the imaging system may serve as an imaging module as part of another standalone system. For example, the imaging system may form a part of an object conveyance system, such as a luggage conveyor belt, for package inspection. In another example, the imaging system may form a part of radiation therapy system. In such a configuration, the radiation therapy system can be configured as a radiotherapy or radiosurgery device that generates a beam of kilovolt (kV) or megavolt (MV) x-ray radiation to treat a region in patient 102. The treatment beam components of the radiation therapy system may be supported on the same gantry 106 as the imaging system 100, or may be supported on a separate structure. The treatment beam may be directed at the patient 102 in between x-ray pulse pairs used for imaging or after completion of a particular imaging sequence. In some cases, treatment may occur during imaging, assuming safeguards are put in place to prevent distortion of the image due to additional x-rays received by the imager 112 from the treatment beam.

Figure 8:
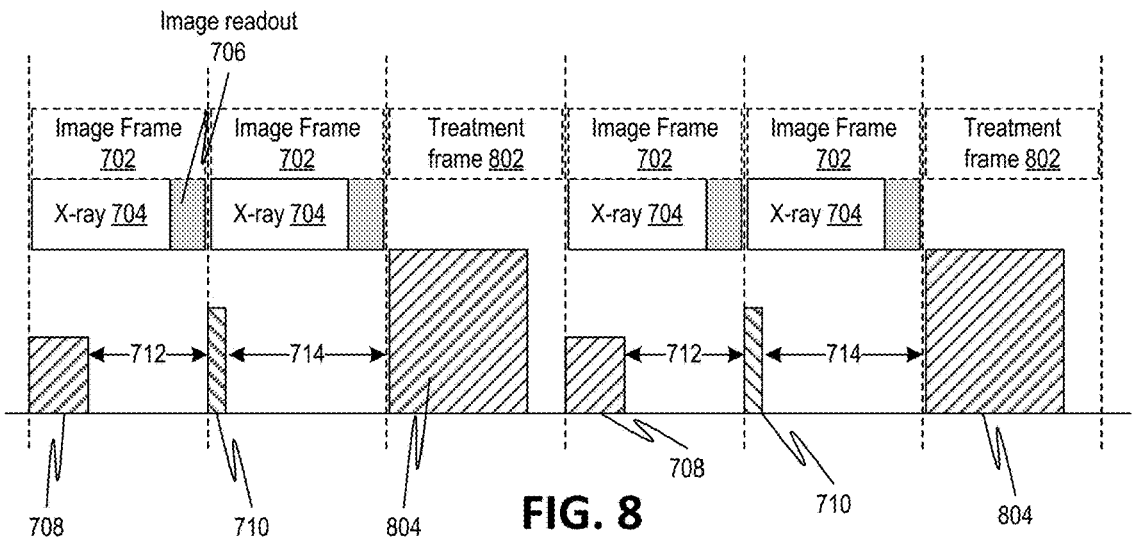
FIG. 8 is a timing diagram illustrating a timing scheme of dual energy imaging interlaced with irradiation pulses for effecting a radiation treatment, according to embodiments of the disclosed subject matter.

For example, FIG. 8 shows an example of a pulse train of low energy pulses 708 and high energy pulses 710, with a MV therapy beam 804 in a treatment frame 802 interlaced between the kV imaging pulse pairs. The treatment frame 802 may be immediately after the last image frame 702 of the pulse pair, or it may be delayed after the last image frame to allow for sufficient time for image processing and output, as well as any time for image analysis for locating the desired target (e.g., tumor) in the image. Thus, the GIB-based system can be used to rapidly image the patient using multiple energies (i.e., pulses 708 and 710) in order to better visualize and delineate the tumor in the patient. The information obtained from the resulting image can be used to modify the treatment beam (e.g., the linac radiation map) to be more accurate. As a result, the treatment system can deliver a more precise dose to the tumor while sparing the surrounding healthy tissue from unnecessary radiation. The GIB can control not only the imaging but can instruct the treatment system as well to modify the therapy plan on the fly.

In a non-limiting example, the imaging system is used for visualizing lung tumors in real-time, which tumors would otherwise be obstructed by overlying ribs. Such visualization can be particularly important in monitoring x-ray delivery during radiation therapy to the lung tumor. The imaging system can thus allow real-time or near real-time (i.e., less than is later) monitoring of any changes in the location of the tumor, for example, due to breathing induced motion or other patient, since the original therapy plan was made.

Although much of the above noted description discusses dual-energy x-ray imaging using pulse pairs having a first higher energy and a second lower energy, embodiments of the disclosed subject matter also include more than two energy levels. For example, in a three energy x-ray imaging system, a pulse set having first through third successive pulses of different energy levels (e.g., high, intermediate, and low) can be used in system 100. Operation of the GIB

202 and other system components may be similar to that discussed with respect to the dual-energy configurations. For example, an x-ray tube for three energies may have three filaments and three grids (similar to that shown in FIGS. 5A-5B) or three filaments with one or two grids (similar to that shown in FIGS. 6A-6B).

Figure 9:
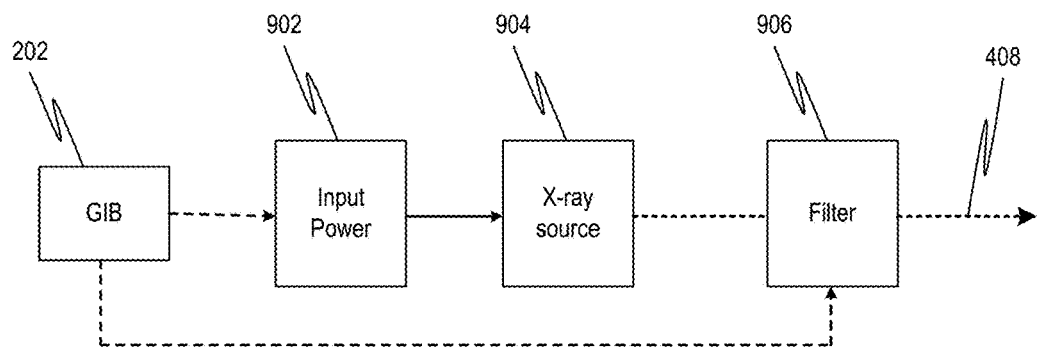
FIG. 9 is a simplified schematic diagram of another x-ray source controlled by a generator interface box, according to embodiments of the disclosed subject matter.

Moreover, although embodiments discussed above have focused on imaging using x-rays of kV energy levels from an x-ray tube, embodiments of the disclosed subject matter are not limited thereto. Indeed, other x-ray sources (e.g., linacs, synchrotrons, etc.) and/or higher x-ray energy levels (e.g., MeV range) are also possible according to one or more contemplated embodiments. FIG. 9 illustrates such a generic configuration where GIB 202 controls the input power 902 to the x-ray source 904 (e.g., an electron gun) similar to the controlling of filament current in the x-ray tube configuration of FIG. 4A. The GIB 202 may also control a filter module 906, for example, by moving individual or combinations of filter elements into the radiation beam path 408 to control the mean energy of the resulting x-rays.

Embodiments of the disclosed subject matter include a GIB that allows for optimization of multi-energy imaging and radiation therapy customization. The GIB allows not only for preloading of pulse parameters for a whole sequence of x-ray pulses, but also is capable of modifying the x-ray output in real-time and pulse to pulse, or to skip pulses as needed while maintaining synchronization between other imaging and radiation treatment system components.

Thus, embodiments of the disclosed GIB may offer one or more the following features:
- change x-ray energy and simultaneously adjust the tube output in terms of tube current (mA) and/or x-ray pulse width (ms), from one pulse to another in a series of imaging pulses;
- control the x-ray tube, generator and x-ray detector using a central controller that keeps all the components synchronized and makes forward looking decisions;
- modify upcoming x-ray pulse parameters on the fly;
- modify pulse parameters in real-time based on imaging characteristics or other signals, such as respiration or gantry rotation signals;
- modify a radiation beam for effecting a treatment in between image frames;
- control and synchronize secondary system components, such as x-ray filters or aperture, with imaging pulses;
- control all, or at least most, of parameters associated with the x-ray beam, including pulse timing, beam current, on-off windows, and filter selection/actuation;
- skip x-ray pulses in a pulse train;
- choose the start and end of x-ray pulses within the imaging time window; and
- modify imaging frame rate.

In one or more first embodiments, a system comprises an x-ray source, an x-ray imager, and a generator interface box. The x-ray source is constructed to generate a series of individual x-ray pulses. The series can include a first x-ray pulse having a first energy level and a subsequent second x-ray pulse having a second energy level different from the first energy level. The x-ray imager is disposed so as to receive x-rays from the x-ray source and to detect the received x-rays for image generation. The generator interface box is configured to control the x-ray source to provide the series of individual x-ray pulses and to synchronize detection by the x-ray imager with generation of the individual x-ray pulses.

In the first embodiments, or any other embodiment, the x-ray source comprises an x-ray tube and a generator for supplying voltage and/or current to the x-ray tube to generate said series of individual x-ray pulses.

In the first embodiments, or any other embodiment, the x-ray source comprises at least one of an x-ray tube, a linear accelerator, a betatron, or a synchrotron.

In the first embodiments, or any other embodiment, the system further comprises a computer processing unit separate from the generator interface box and configured to process signals from the x-ray imager indicative of the detected x-rays to generate one or more images. The computer processing unit can be configured to generate a combined image based on a first image generated from the first x-ray pulse and a second image generated from the second x-ray pulse.

In the first embodiments, or any other embodiment, the generator interface box is configured to control voltage, current, or power input to the x-ray source, and/or timing, pulse width, and/or energy levels of each of the individual x-ray pulses. The generator interface box can control based on at least one of object or anatomy imaged, characteristics of the x-ray source, image quality, a signal indicative of respiratory or cardiac motion of a patient being imaged, and an external input signal.

In the first embodiments, or any other embodiment, the x-ray source is configured to generate the first x-ray pulse during a first image frame and the second x-ray pulse during a second image frame, the x-ray imager is configured to read out during an end period of each image frame, and the generator interface box is configured to control a timing of the first and second x-ray pulses in their respective image frames.

In the first embodiments, or any other embodiment, the first x-ray pulse has a higher energy level than the second x-ray pulse, the first x-ray pulse is adjacent to the end period of the first image frame, and the second x-ray pulse is at a beginning of the second image frame and adjacent to the end period of the first image frame.

In the first embodiments, or any other embodiment, the series of individual x-ray pulses includes a third x-ray pulse generated after the first and second x-ray pulses. The first and third x-ray pulses can have a higher energy level than the second x-ray pulse, and a time period between the first x-ray pulse and the second x-ray pulse is less than a time period between the second x-ray pulse and the third x-ray pulse.

In the first embodiments, or any other embodiment, the series of individual x-ray pulses is a pulse train of alternating first and second pulses, each pulse being generated during a corresponding image frame. The x-ray imager can be configured to read out during a period of each image frame, and the generator interface box can be configured to control a timing of the x-ray pulses within their respective image frames.

In the first embodiments, or any other embodiment, the generator interface box can be configured to skip one or more pulses in the pulse train while maintaining synchronization between the x-ray source and the x-ray imager.

In the first embodiments, or any other embodiment, the system further comprises a filter module having one or more selectable filter elements to alter characteristics of an x-ray pulse passing therethrough. The generator interface box can also control the filter module together with the x-ray source in generating the series of individual x-ray pulses.

In the first embodiments, or any other embodiment, the x-ray source comprises an x-ray tube with at least two filaments and a generator for supplying voltage and/or current to the x-ray tube to generate the first and second x-ray pulses. The generator is configured to hold each filament at working current during and between generation of the first and second x-ray pulses.

In the first embodiments, or any other embodiment, the x-ray tube comprises a grid disposed adjacent to one of the at least two filaments, and the generator interface box is configured to control a voltage of the grid to be a first voltage that repels electrons from an anode of the x-ray tube when generating the second x-ray pulse and to be a second voltage that electrons to pass to the anode when generating the first x-ray pulse.

In the first embodiments, or any other embodiment, each filament of the x-ray tube has a respective grid controllable by the generator interface box and constructed to alter an energy of the x-ray pulse formed by electrons from the filaments impacting an anode of the x-ray tube.

In the first embodiments, or any other embodiment, the system further comprises a radiation therapy module for delivering kilovolt (kV) or megavolt (MV) energy to treat a patient.

In one or more second embodiments, a method comprises using a generator interface box to control an x-ray source to generate a series of individual x-ray pulses during respective image frames and to synchronize image readout by an x-ray imager with a readout period of each image frame. The series can include at least a first x-ray pulse and a second x-ray pulse having a different energy level than that of the first x-ray pulse. The method can further comprise using a computer processing unit to process signals from the x-ray imager during respective image frames to generate one or more images of a patient or object through which the first and second x-ray pulses have passed.

In the second embodiments, or any other embodiment, the x-ray source comprises an x-ray tube, a linear accelerator, a betatron, or a synchrotron.

In the second embodiments, or any other embodiment, the controlling can include one or more of controlling timing of x-ray pulses within respective image frames; controlling pulse widths of the x-ray pulses; controlling energy levels of each x-ray pulse; controlling voltage, current, or power input to the x-ray source; and skipping generation of one or more x-ray pulses.

In the second embodiments, or any other embodiment, the controlling and synchronizing using the generator interface box is responsive to at least one of object or anatomy imaged, characteristics of the x-ray source, characteristics of the image, image quality, a signal indicative of respiratory or cardiac motion of a patient being imaged, and an external input signal.

In the second embodiments, or any other embodiment, the first x-ray pulse has a higher energy level than the second x-ray pulse, the first x-ray pulse has a pulse width less than that of the second x-ray pulse, and a time period between the first x-ray pulse and the second x-ray pulse is substantially equal to the readout period.

In the second embodiments, or any other embodiment, the method further comprises, using the generator interface box, controlling the filter module to have a first configuration during generation of the first x-ray pulse and to have a second configuration during generation of the second x-ray pulse. The filter module can have one or more selectable filter elements to alter characteristics of x-rays passing therethrough.

In the second embodiments, or any other embodiment, the x-ray source comprises an x-ray tube with at least two filaments, and the method further comprises maintaining each filament of the x-ray tube at working current during and between the first and second x-ray pulses. The method also comprises, during generation of one of the first and second x-ray pulses, applying a first voltage to a grid disposed adjacent to one the filaments of the x-ray tube such that the grid repels electrons from an anode of the x-ray tube, and during generation of the other of the first and second x-ray pulses, applying a second voltage to the grid such that electrons pass to the anode.

In the second embodiments, or any other embodiment, the method further comprises delivering kilovolt (kV) or megavolt (MV) energy to the patient to effect a radiation therapy.

In one or more third embodiments, there is provided a non-transitory computer-readable storage medium, upon which is embodied a sequence of programmed instructions for x-ray imaging, and a computer processing system that executes the sequence of programmed instructions embodied on the computer-readable storage medium to cause the computer processing system to execute the method of the second embodiments, or any other embodiment.

It will be appreciated that the aspects of the disclosed subject matter can be implemented, fully or partially, in hardware, hardware programmed by software, software instruction stored on a computer readable medium (e.g., a non-transitory computer readable medium), or any combination of the above. For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

It is thus apparent that there is provided, in accordance with the present disclosure, systems, methods, and devices for multi-energy x-ray imaging. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A system comprising:
   an x-ray source constructed to generate a series of individual x-ray pulses, the series including at least a first x-ray pulse having a first energy level and a second x-ray pulse having a second energy level different from the first energy level;
   an x-ray imager disposed so as to receive x-rays from the x-ray source and to detect the received x-rays for image generation; and
   a generator interface box configured to control the x-ray source to provide the series of individual x-ray pulses and to synchronize detection by the x-ray imager with generation of the individual x-ray pulses,
   wherein
   the x-ray source is configured to generate the first x-ray pulse during a first image frame and the second x-ray pulse during a second image frame,
   the x-ray imager is configured to read out the first x-ray pulse during and end period of the first image frame and the second x-ray pulse during an end period of the second image frame, and
   the generator interface box is configured to control a timing of the first and second x-ray pulses in their respective image frames,
   wherein the generator interface box is further configured to simultaneously control parameters associated with an x-ray beam resulting from the series of individual x-ray pulses, and
   wherein the image generation includes generating an image of a patient or object through which the x-ray beam resulting from the series of individual x-ray pulses has passed.

2. The system of claim 1, wherein the x-ray source comprises:
   an x-ray tube and a generator for supplying voltage and/or current to the x-ray tube to generate said first and second x-ray pulses;
   a linear accelerator;
   a betatron; or
   a synchrotron.

3. The system of claim 1, further comprising a computer processing unit separate from the generator interface box and configured to process signals from the x-ray imager indicative of the detected x-rays to generate one or more images.

4. The system of claim 1, wherein said parameters controlled by the generator interface box include:
   voltage, current, or power input to the x-ray source; and/or
   timing, pulse width, and/or energy levels of each of the individual x-ray pulses.

5. The system of claim 4, wherein the generator interface box controls based on at least one of object or anatomy imaged, characteristics of the x-ray source, image quality, a signal indicative of respiratory or cardiac motion of the patient being imaged, and an external input signal.

6. The system of claim 1, wherein
   the first x-ray pulse has a higher energy level than the second x-ray pulse,
   the first x-ray pulse is adjacent to the end period of the first image frame, and
   the second x-ray pulse is at a beginning of the second image frame and adjacent to the end period of the first image frame.

7. The system of claim 1, wherein
the series of individual x-ray pulses is a pulse train of alternating first and second pulses, each pulse being generated during a corresponding image frame,
the generator interface box is configured to control a timing of the x-ray pulses within their respective image frames.

8. The system of claim 7, wherein the generator interface box adjusts characteristics for a pair of first and second pulses to be generated based on a current image frame or a prior image frame.

9. The system of claim 7, wherein the generator interface box is configured to skip one or more pulses in the pulse train while maintaining synchronization between the x-ray source and the x-ray imager.

10. The system of claim 1, further comprising a radiation therapy module for delivering kilovolt (kV) or megavolt (MV) energy to treat the patient.

11. A method comprising:
using a generator interface box, controlling an x-ray source to generate a series of individual x-ray pulses during respective image frames, the series including at least a first x-ray pulse generated during a first image frame and a subsequent second x-ray pulse having a different energy level than that of the first x-ray pulse generated during a second image frame;
using the generator interface box, controlling a timing of the first and second x-ray pulses in their respective image frames and synchronizing image readout by an x-ray imager with a readout period of each image frame so as to read out the first x-ray pulse during an end period of the first image frame and the second x-ray pulse during an end period of the second image frame; and
using a computer processing unit, processing signals from the x-ray imager during respective image frames to generate one or more images of a patient or object through which the first and second x-ray pulses have passed.

12. The method of claim 11, wherein the x-ray source comprises an x-ray tube, a linear accelerator, a betatron, or a synchroton.

13. The method of claim 11, wherein the controlling includes one or more of:
controlling timing of x-ray pulses within respective image frames;
controlling pulse widths of the x-ray pulses;
controlling energy levels of each x-ray pulse;
controlling voltage, current, or power input to the x-ray source; and
skipping generation of one or more x-ray pulses.

14. The method of claim 11, wherein the controlling and synchronizing using the generator interface box is responsive to at least one of object or anatomy imaged, characteristics of the x-ray source, characteristics of the image, image quality, a signal indicative of respiratory or cardiac motion of a patient being imaged, and an external input signal.

15. The method of claim 11, wherein
the first x-ray pulse has a higher energy level than the second x-ray pulse,
the first x-ray pulse has a pulse width less than that of the second x-ray pulse, and
a time period between the first x-ray pulse and the second x-ray pulse is substantially equal to the readout period.

16. The method of claim 15, further comprising delivering kilovolt (kV) or megavolt (MV) energy to the patient to effect a radiation therapy.

17. A non-transitory computer-readable storage medium upon which is embodied a sequence of programmed instructions for x-ray imaging, and a computer processing system that executes the sequence of programmed instructions embodied on the computer-readable storage medium to cause the computer processing system to:
control an x-ray source to generate a series of individual x-ray pulses during respective image frames, the series including at least a first x-ray pulse generated during a first image frame and a subsequent second x-ray pulse having a different energy level than that of the first x-ray pulse generated during a second image frame;
control a timing of the first and second x-ray pulses in their respective image frames and synchronize image readout by an x-ray imager with a readout period of each image frame so as to read out the first x-ray pulse during an end period of the first image frame and the second x-ray pulse during an end period of the second image frame; and
processing signals from the x-ray imager during the respective image frames to generate one or more images of a patient or object through which the first and second x-ray pulses have passed.

18. The non-transitory computer-readable storage medium and computer processing system of claim 17, wherein controlling the x-ray source comprises one or more of:
controlling timing of x-ray pulses within respective image frames;
controlling pulse widths of the x-ray pulses;
controlling energy levels of each x-ray pulse;
controlling voltage, current, or power input to the x-ray source; and
skipping generation of one or more x-ray pulses.

19. The non-transitory computer-readable storage medium and computer processing system of claim 17, wherein the execution of the sequence of programmed instructions further causes the computer processing system to control the x-ray source and synchronize image readout based on at least one of the object or anatomy imaged, characteristics of the x-ray source, characteristics of the image, image quality, a signal indicative of respiratory or cardiac motion of the patient being imaged, and an external input signal.

20. A system comprising:
an x-ray source constructed to generate a series of individual x-ray pulses, the series including at least a first x-ray pulse having a first energy level and a second x-ray pulse having a second energy level different from the first energy level;
an x-ray imager disposed so as to receive x-rays from the x-ray source and to detect the received x-rays for image generation; and
a generator interface box configured to control the x-ray source to provide the series of individual x-ray pulses and to synchronize detection by the x-ray imager with generation of the individual x-ray pulses,
wherein the generator interface box is further configured to simultaneously control parameters associated with an x-ray beam resulting from the series of individual x-ray pulses,
wherein
the x-ray source is configured to generate the first x-ray pulse during a first image frame and the second x-ray pulse during a second image frame,
the x-ray imager is configured to read out the first x-ray pulse during an end period of the first image frame and the second x-ray pulse during an end period of the second image frame, and the generator interface box is configured to control a timing of the first and second x-ray pulses in their respective image frames, and wherein the first x-ray pulse has a higher energy level than the second x-ray pulse, the first x-ray pulse is adjacent to the end period of the first image frame, and the second x-ray pulse is at a beginning of the second image frame and adjacent to the end period of the first image frame.

* * * * *